(12) United States Patent
Sankai

(10) Patent No.: US 11,980,751 B2
(45) Date of Patent: May 14, 2024

(54) CARDIAC OUTPUT SUPPORT APPARATUS

(71) Applicants: CYBERDYNE INC., Tsukuba (JP); UNIVERSITY OF TSUKUBA, Tsukuba (JP)

(72) Inventor: Yoshiyuki Sankai, Tsukuba (JP)

(73) Assignees: CYBERDYNE INC., Ibaraki (JP); UNIVERSITY OF TSUKUBA, Ibaraki (JP)

( * ) Notice: Subject to any disclaimer, the term of this patent is extended or adjusted under 35 U.S.C. 154(b) by 606 days.

(21) Appl. No.: 17/271,968

(22) PCT Filed: Aug. 30, 2019

(86) PCT No.: PCT/JP2019/034226
§ 371 (c)(1),
(2) Date: Feb. 26, 2021

(87) PCT Pub. No.: WO2020/045654
PCT Pub. Date: Mar. 5, 2020

(65) Prior Publication Data
US 2021/0338998 A1    Nov. 4, 2021

(30) Foreign Application Priority Data

Aug. 30, 2018  (JP) ................................ 2018-162211

(51) Int. Cl.
*A61M 60/00* (2021.01)
*A61M 60/191* (2021.01)
(Continued)

(52) U.S. Cl.
CPC ........ *A61M 60/191* (2021.01); *A61M 60/289* (2021.01); *A61M 60/468* (2021.01); *A61M 2205/04* (2013.01)

(58) Field of Classification Search
CPC .............. A61M 60/191; A61M 60/289; A61M 60/468; A61M 60/839
See application file for complete search history.

(56) References Cited

U.S. PATENT DOCUMENTS 4,690,134 A * 9/1987 Snyders ............... A61M 60/839
601/153
6,063,115 A * 5/2000 Gealow ................ A61M 60/878
623/3.12
(Continued)

FOREIGN PATENT DOCUMENTS

JP    10-174713 A    6/1998
JP    10-174714 A    6/1998
(Continued)

OTHER PUBLICATIONS

International Search Report, PCT/JP2019/034226, dated Oct. 21, 2019, 2 pgs.

*Primary Examiner* — Eric D. Bertram
(74) *Attorney, Agent, or Firm* — Volpe Koenig

(57) ABSTRACT

A first drive unit, in a state where a top end of a tubular joint is interposed into a chest of a target person and is located at a lower heart part, pushes a diaphragm out from the top end of the tubular joint while pressing a gas into the diaphragm, and simultaneously causes the diaphragm to start flexing to cover and wrap the lower heart part, and then stops pressing the gas into the diaphragm at a time point where compression balloons are positioned at atriums and ventricles of a heart, respectively; and second drive units support a pumping function of the heart by alternately repeating an ejecting operation to fill each of the compression balloons with a fluid and cause each compression balloon to expand and an absorbing operation to cause each compression balloon to discharge the fluid and contract.

8 Claims, 7 Drawing Sheets

(51) Int. Cl.
    *A61M 60/289* (2021.01)
    *A61M 60/468* (2021.01)

(56) References Cited

U.S. PATENT DOCUMENTS

| | | | |
|---|---|---|---|
| 6,432,039 B1 | 8/2002 | Wardle | |
| 6,540,659 B1 * | 4/2003 | Milbocker | A61M 60/873 |
| | | | 600/16 |
| 9,220,824 B2 * | 12/2015 | Wildhirt | A61M 60/867 |
| 10,130,456 B2 * | 11/2018 | Wildhirt | A61M 60/839 |
| 10,391,216 B2 * | 8/2019 | Wildhirt | A61M 60/554 |
| 11,382,752 B2 * | 7/2022 | McGuckin, Jr. | A61F 2/2481 |
| 2002/0065449 A1 * | 5/2002 | Wardle | A61F 2/2481 |
| | | | 600/37 |
| 2006/0184048 A1 | 8/2006 | Saadat | |
| 2010/0152523 A1 * | 6/2010 | MacDonald | A61M 60/427 |
| | | | 600/16 |
| 2010/0256441 A1 * | 10/2010 | Lu | A61M 60/191 |
| | | | 600/16 |
| 2011/0172697 A1 | 7/2011 | Jonsson | |
| 2011/0196476 A1 | 8/2011 | Forsell | |
| 2014/0194669 A1 * | 7/2014 | Wildhirt | A61M 60/468 |
| | | | 600/16 |
| 2014/0194717 A1 * | 7/2014 | Wildhirt | A61B 5/6869 |
| | | | 600/509 |

FOREIGN PATENT DOCUMENTS

| | | |
|---|---|---|
| JP | 2002-532189 A | 10/2002 |
| JP | 2011-500295 A | 1/2011 |
| JP | 2011-152449 A | 8/2011 |
| JP | 2012-502679 A | 2/2012 |
| JP | 2017-094157 A | 6/2017 |

* cited by examiner

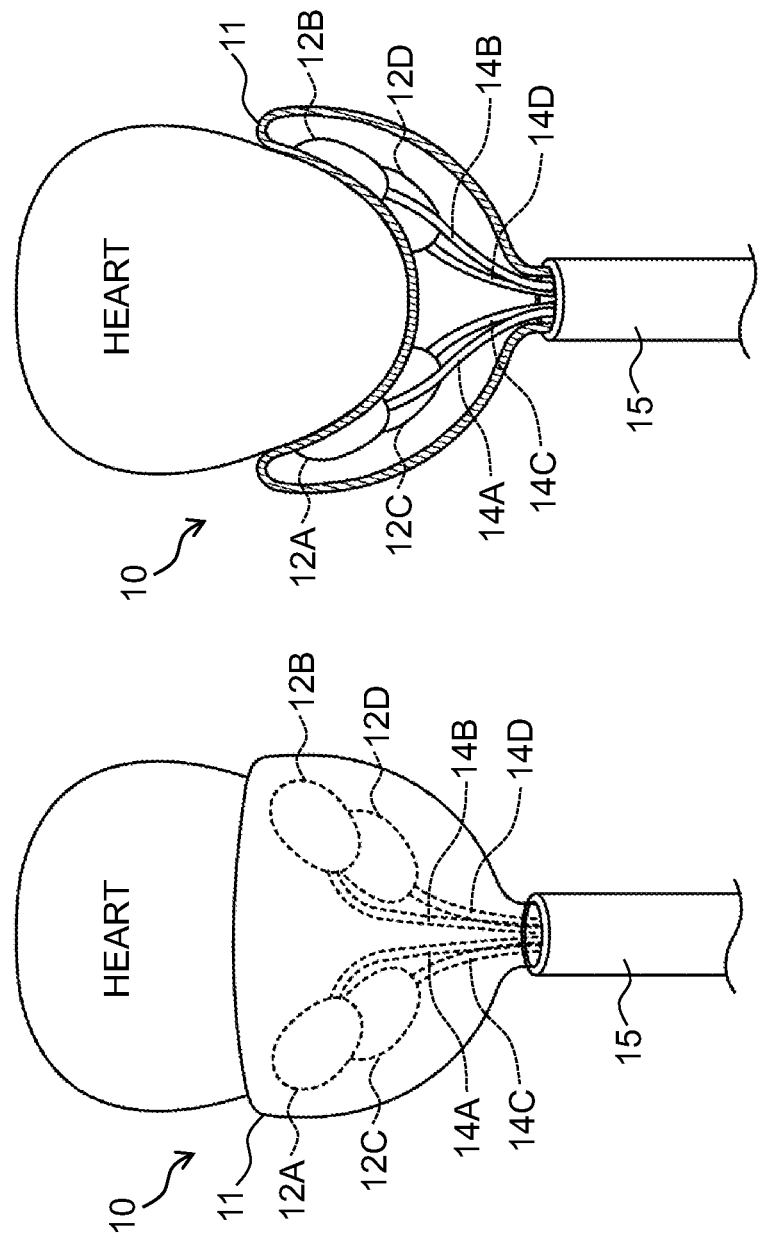

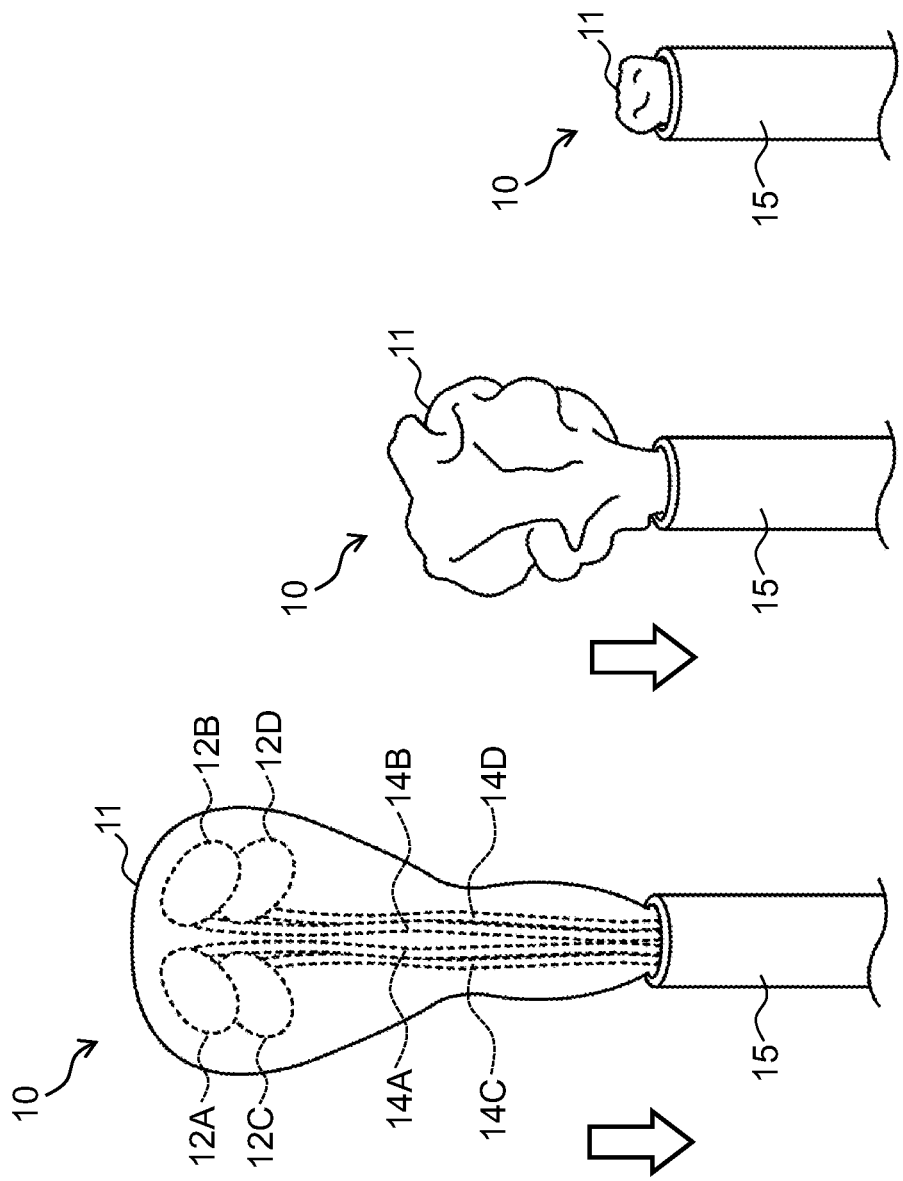

CARDIAC OUTPUT SUPPORT APPARATUS

TECHNICAL FIELD

The present invention relates to a technology for directly compressing a patient's heart whose cardiac output function has significantly deteriorated due to a myocardial infarction.

BACKGROUND ART

The myocardial infarction which is a heart disease is a disease which causes necrosis of cardiac muscles as blood flows to cardiac muscles are obstructed by stenosis or blockage of coronary arteries. A patient who suffers from an acute myocardial infarction often has cardiac arrest within approximately one hour after the occurrence of subjective symptoms, so that it is extremely important to make the blood flows to the entire body promptly resumed.

A conventional method of treating the acute myocardial infarction patient is to deal with the situation sequentially by performing emergency transport at the time of discovery of the subjective symptoms such as chest pain, deciding treatment policies, preparing for a surgery, and making arrangements for cardiovascular surgery medical specialists. However, it is sometimes difficult to give proper treatment in a short time.

In many cases, a Percutaneous Cardiopulmonary Support (PCPS) device to resume the blood flows to the entire body and a treatment to support blood circulation by open chest cardiac massage are employed. This Percutaneous Cardiopulmonary Support device can be attached via a surgical operation conducted by a doctor who is not a cardiovascular surgery medical specialist; however, there are risks of inducing complications such as shortage of an auxiliary flow rate, blood clots, and lower extremity ischemia. Moreover, the open chest cardiac massage has a high cardiac output effect, but requires considerable skills regarding power adjustment and cardiac output cycles.

Consequently, when providing life support to the myocardial infarction patient immediately after the emergency transport, there is required a system for supporting the heart's pumping function without conducting a surgery of the heart.

There is provided an apparatus for treating a heart trouble and the apparatus includes: a confined structure to surround a substantial portion of a patient's heart; a first expansion pocket that applies a pressure to a left ventricle of the heart during a part of a pumping cycle of the heart; and a second expansion pocket that applies a pressure to a right ventricle of the heart during a part of the pumping cycle of the heart, wherein the pressures imparted by the first and second expansion pockets can be independently controlled so that the different pressures are selectively applied to the left ventricle and the right ventricle (see PTL 1).

Moreover, there is proposed a heart compression system configured so that first and second expandable balloons are attached at fixed positions on an inner surface of an outer shell which is manufactured and customized to make its shape substantially fit a part of an outline of a heart at the end of a diastole, which is acquired by an imaging system; and the first and second expandable balloons expand to compress a left ventricle free wall and a right ventricle free wall, respectively, in a state where the outer shell is naturally positioned in a pericardium space (see PTL 2).

Furthermore, there is proposed an implantable device for improving the heart's pumping function by causing the pumping function to work by using a hydraulic system in order to make piston reciprocating motions operate respectively so that first and second chambers which are adapted to retain a liquid pressure are pressure-controlled with respect to a heart contact member which is adapted to make an external force act on a left ventricle and a right ventricle, respectively, of a patient's heart (see PTL 3).

CITATION LIST

Patent Literature

PTL 1: Japanese Unexamined Patent Application Publication (Translation of PCT Application) No. 2002-532189
PTL 2: Japanese Unexamined Patent Application Publication (Translation of PCT Application) No. 2011-500295
PTL 3: Japanese Patent Application Laid-Open (Kokai) Publication No. 2017-94157

SUMMARY OF THE INVENTION

Problems to be Solved by the Invention

Meanwhile, PTL 1 has the confined structure, which uses a biocompatible material such as silicone or polyurethane, to surround the substantial portion of the heart; and although it has flexibility, it is necessary to perform a thoracotomy by opening a chest of the target person along the length equal to or longer than the width of their heart in order to locate the apparatus at the heart.

Moreover, regarding PTL 2, soft-fixation of the outer shell, which is a non-interfering sac, to the heart is conducted, that is, the outer shell is brought into close contact with, and thereby placed along, the heart; however, in this case as well similarly to PTL1, it is necessary to perform the thoracotomy by opening the chest of the target person along the length equal to or longer than the width of their heart.

Furthermore, regarding PTL 3, the heart contact member is made of a ceramic material or a carbon material and is embedded in the body together with a fixing member adapted to be fixed to, for example, the patient's breastbone or ribs; and, therefore, in this case as well similarly to the aforementioned PTL 1 and PTL 2, it is necessary to perform the thoracotomy by opening the chest of the target person along the length equal to or longer than the width of their heart.

Consequently, each one of the aforementioned PTL 1 to PTL 3 is required to perform the thoracotomy by opening the chest of the target person along the length equal to or longer than the width of their heart when placing the apparatus having the heart pumping support function at the patient's heart, so that the problem of heavy physical burden on the target person remains.

The present invention was devised in consideration of the above-described circumstances and proposes a cardiac output support apparatus capable of providing life support to the target person by significantly reducing the physical burden on the target person.

Means to Solve the Problems

In order to solve the above-described problem, provided according to the present invention is a cardiac output support apparatus including: a diaphragm whose size is set to fit an external shape of a lower heart part of a target person and which is composed of a flexible membrane that is responsive to a gas pressure; a plurality of compression balloons which are pasted at specified positions of an inner wall surface of the diaphragm so that the compression balloons are positioned opposite atriums and ventricles of a heart, respectively, when the lower heart part is covered and wrapped with the diaphragm; a first drive unit that is driven to press gas into the diaphragm; second drive units that are driven to eject or absorb a fluid to or from the compression balloons, respectively; and a tubular joint with a hollow part in which the diaphragm and each of the compression balloons are collectively stuffed, wherein the first drive unit, in a state where a top end of the tubular joint is interposed in a chest of the target person and is located at the lower heart part, pushes the diaphragm out from the top end of the tubular joint while pressing the gas into the diaphragm, and simultaneously causes the diaphragm to start flexing to cover and wrap the lower heart part, and then stops pressing the gas into the diaphragm at a time point where the compression balloons are positioned at the atriums and the ventricles of the heart, respectively; and wherein the second drive units support a pumping function of the heart by alternately repeating an ejecting operation to fill each of the compression balloons with the fluid and cause each compression balloon to expand and an absorbing operation to cause each compression balloon to discharge the fluid and contract.

As a result, regarding the cardiac output support apparatus, the target person's chest is incised along the length approximately equal to a diameter of the tubular joint; and by increasing a gas pressure inside the diaphragm from outside in a state where the tubular joint is inserted into the incised part, the lower heart part can be covered and wrapped with the diaphragm and simultaneously each compression balloon can be positioned. Consequently, if the cardiac output support apparatus is employed, it is no longer necessary to incise the target person's chest along the length equal to or longer than the width of the heart and the physical burden on the target person can be reduced significantly.

Moreover, according to the present invention, a peripheral region of the diaphragm which does not enter into direct contact with the heart when covering and wrapping the lower heart part is formed of a material having flexibility and non-pliability. As a result, when each compression balloon is filled with the fluid and expands, the cardiac output support apparatus prevents the peripheral region of the diaphragm from expanding towards outside around the heart and compressing the surroundings of the target person's heart.

Furthermore, according to the present invention, a whole or part of an exposed portion of each compression balloon other than its abutting region in contact with the diaphragm is formed of a material having flexibility and non-pliability. As a result, when each compression balloon is filled with the fluid and expands, each compression balloon itself expands only in a direction opposite the diaphragm; and, therefore, the cardiac output support apparatus can prevent the peripheral region of the diaphragm from expanding towards outside around the heart and avoid any compression on the surroundings of the target person's heart.

Furthermore, according to the present invention, an arterial blood measurement unit that measures a pulse rate and arterial oxygen saturation of the target person is further included, wherein each of the second drive units independently adjusts a cardiac output and a cardiac output cycle with respect to each compression balloon in accordance with a measurement result of the arterial blood measurement unit. As a result, the cardiac output support apparatus can control each compression balloon in accordance with a blood circulation state of the target person and it becomes possible to suppress degradation of the heart's pumping function (a blood receiving function and a blood sending function) while letting the atriums and the ventricles of the heart contract or relax.

Furthermore, according to the present invention, a cardiac condition detection unit that detects a disease condition of the heart of the target person is further included, wherein each of the second drive units independently controls each compression balloon in a specified cardiac output cycle and with a specified cardiac output on the basis of a detection state of the cardiac condition detection unit. As a result, the cardiac output support apparatus can control each compression balloon in accordance with the disease condition of the target person's heart and it becomes possible to suppress the degradation of the heart's pumping function while letting the atriums and the ventricles of the heart contract or relax.

Furthermore, according to the present invention, the diaphragm is stuffed into the hollow part of the tubular joint with reference to a mark assigned to the top end of the tubular joint by defining a positional relationship between the respective compression balloons; and when the top end of the tubular joint is located at the lower heart part, the mark is positioned in conformity with positions of the atriums and the ventricles. As a result, when a doctor or the like inserts the tubular joint into the target person's chest, the cardiac output support apparatus can easily position the respective compression balloons at the atriums and the ventricles of the heart after filling the diaphragm with air simply by positioning the tubular joint at the lower heart part with reference to the mark.

Furthermore, according to the present invention, a freely expandable and contractable mesh-like material whose size is set to fit the external shape of the lower heart part of the target person is made to cover and wrap the lower heart part in such a manner that coronary arteries are exposed from gaps under an environment of X-ray imaging; and the diaphragm is made to further cover and wrap a surface of the mesh-like material. As a result, when the target person's lower heart part which is covered and wrapped with the mesh-like material is covered and wrapped with the diaphragm and the internal air pressure is increased, it is possible to avoid the occurrence of any damage due to compression on the coronary arteries of the lower heart part even if the ejecting operation and the absorbing operation by each compression balloon are performed.

Advantageous Effects of the Invention

The cardiac output support apparatus capable of providing life support to the target person by significantly reducing physical burden on the target person can be implemented as described above according to the present invention.

BRIEF DESCRIPTION OF DRAWINGS

FIGS. 1A and 1B are a configuration diagram of a pumping function unit according to this embodiment;

FIGS. 2A-2C are a schematic diagram illustrating a process of stuffing a diaphragm and each compression balloon into a tubular joint in a pumping function unit in FIG. 1;

DESCRIPTION OF EMBODIMENTS

Figure 3D:
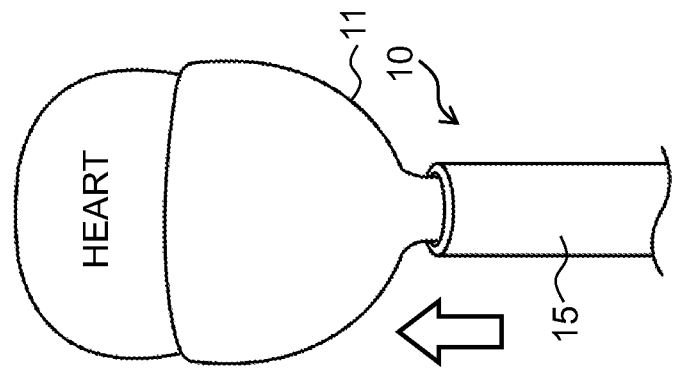
FIGS. 3A-3D are a schematic diagram for explaining a state where the pumping function unit in FIG. 1 is mounted at a lower heart part.

An embodiment of the present invention will be described below in detail with reference to the drawings.

(1) Configuration of Pumping Function Unit

Referring to FIG. 1A and FIG. 1B, a pumping function unit 10 is configured of: a diaphragm 11 made of a flexible membrane whose size is set to fit an external shape of a lower heart part of a target person (such as a patient whose cardiac output function has degraded significantly due to a myocardial infarction); four compression balloons 12A to 12D which are respectively pasted at specified positions on an inner wall surface of the diaphragm 11; and a tubular joint 15 that bundles and receives an air supply passage 13, which communicates with an end of the diaphragm 11 and tubes 14A to 14D which are drawn from the respective compression balloons 12A to 12D.

The tubular joint 15 has a hollow part into which the diaphragm 11 and the respective compression balloons 12A to 12D are collectively stuffed; and the diaphragm 11 and the respective compression balloons 12A to 12D are designed to expand and be discharged from the top end side of the tubular joint 15 by increasing an air pressure inside the diaphragm 11.

The respective compression balloons 12A to 12D are pasted respectively at specified positions on an inner wall surface of the diaphragm 11 so that they are positioned opposite right and left atriums and ventricles, respectively, when the lower heart part is covered and wrapped with the diaphragm 11.

Under this circumstance, the diaphragm 11 is designed so that its entire membrane flexes according to the air pressure; however, a material with a very low degree of expansion and contraction (that is, a low modulus of elasticity) is selected. Examples of a desired material to be selected include organic or inorganic polymeric fiber materials and polymeric conjugated fiber materials which have no property causing damage to a living body. Artificial leather, imitation leather, or synthetic leather can also be applied as long as they have no property causing damage to a living body.

The respective compression balloons 12A to 12D are formed of, for example, silicone rubber and are designed to expand or contract as caused by water discharged or absorbed via the tubes 14A to 14D from second drive units 23A to 23D (FIG. 4) described later.

Practically, with the pumping function unit 10 as illustrated in FIG. 2A to FIG. 2C, the diaphragm 11 and the respective compression balloons 12A to 12D are stuffed into the hollow part of the tubular joint 15 in advance. When doing so, the diaphragm 11 is stuffed into the hollow part of the tubular joint 15 with reference to a mark assigned to the top end of the tubular joint 15 by defining a positional relationship between the respective compression balloons 12A to 12D; and when locating the top end of the tubular joint 15 at the lower heart part, the mark is positioned in conformity with the positions of the right and left ventricles.

As a result, when a doctor or the like inserts the tubular joint 15 to attach the pumping function unit 10 to the target person's chest, they can easily position the respective compression balloons 12A to 12D at the right and left atriums and ventricles of the heart after filling the diaphragm 11 with air simply by positioning them at the lower heart part with reference to the mark.

Figure 3C:
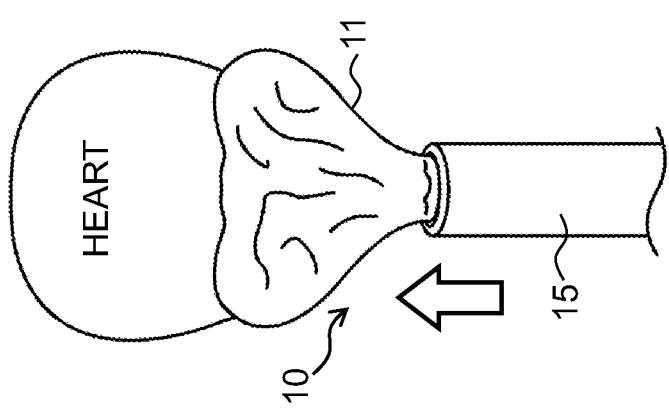
Figure 3B:
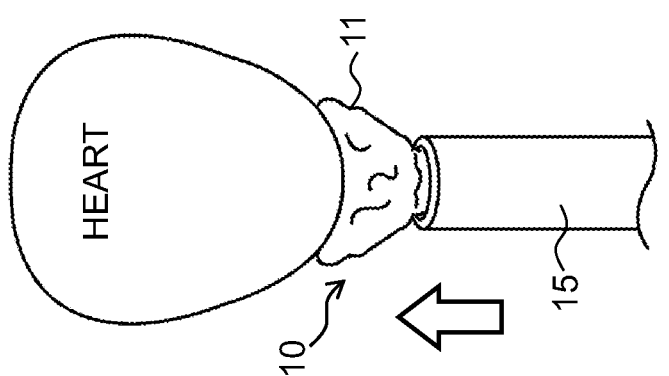
Figure 3A:
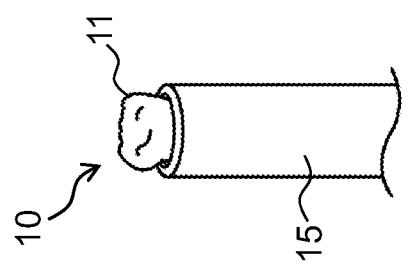

Specifically speaking, regarding the pumping function unit 10, when the top end of the tubular joint 15 (FIG. 3A), in which the diaphragm 11 and the respective compression balloons 12A to 12D are stuffed, is located at the target person's lower heart part (FIG. 3B), the first drive unit 22 (FIG. 4) described later starts to press air into the diaphragm 11 and the lower heart part is gradually covered and wrapped with the diaphragm 11 (FIG. 3C). Subsequently, when the diaphragm 11 covers and wraps the lower heart part and the respective compression balloons 12A to 12D are positioned at the right and left atriums and ventricles of the heart, pressing the air into the diaphragm 11 is stopped (FIG. 3D).

Incidentally, when the diaphragm 11 covers and wraps the lower heart part and the respective compression balloons 12A to 12D are positioned at the right and left atriums and ventricles of the heart at the target person's lower heart part and if the actual respective compression balloons 12A to 12D are deviated from the positions of the right and left atriums and ventricles of the heart even though they were positioned with reference to the aforementioned mark, the doctor or the like may adjust the positions of the compression balloons 12A to 12D corresponding to the right and left atriums and ventricles under the X-ray environment.

(2) Overall Configuration of Cardiac Output Support Apparatus

Figure 4:
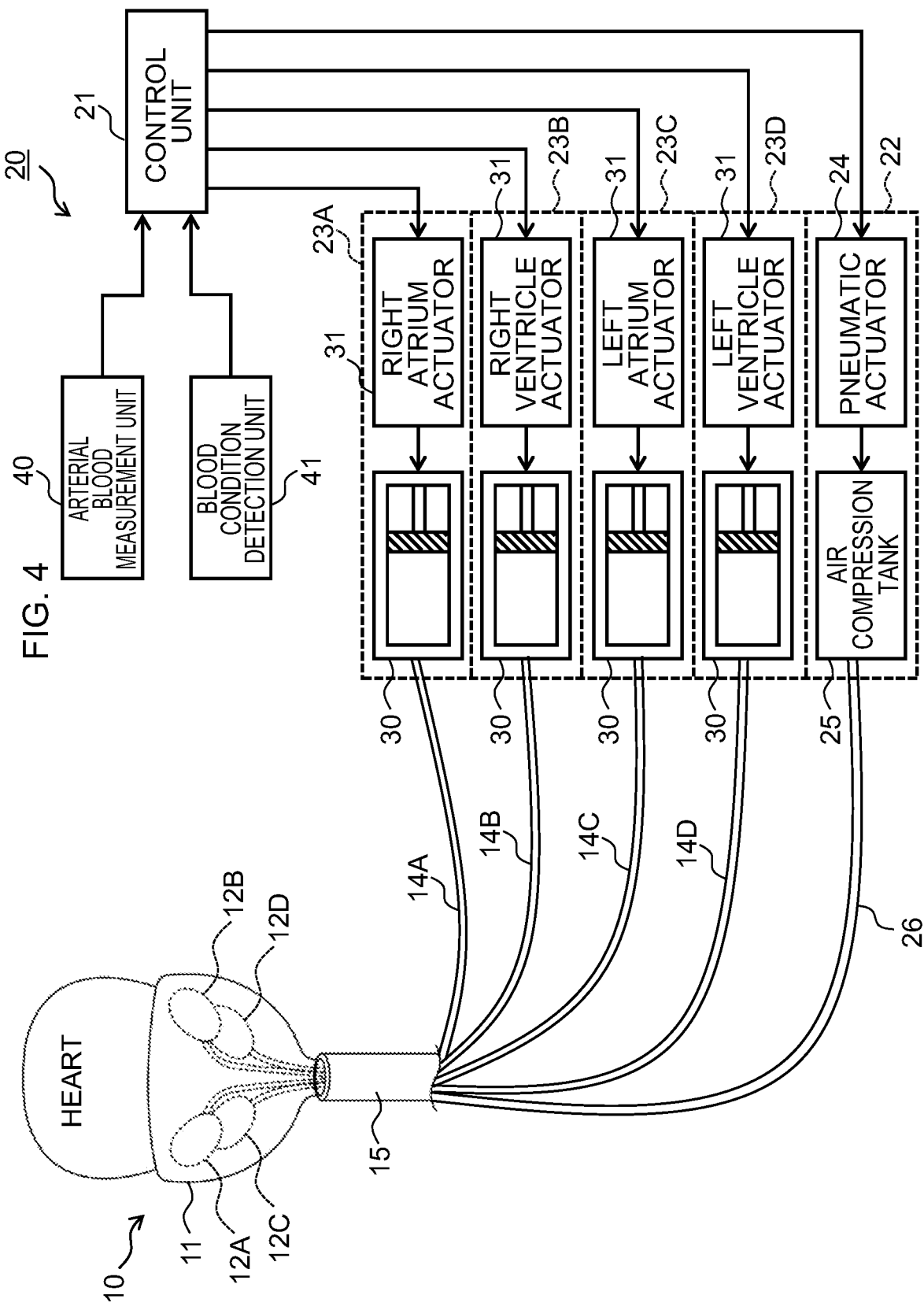
FIG. 4 is a block diagram illustrating an overall configuration of a cardiac output support apparatus according to this embodiment.

FIG. 4 illustrates an overall configuration of a cardiac output support apparatus 20. The cardiac output support apparatus 20 includes: a control unit 21 that controls the entire apparatus; the pumping function unit 10 that supports the pumping function of the target person's heart; and the first drive unit 22 and the second drive units 23A to 23D that drive the diaphragm 11 and the respective compression balloons 12A to 12D, respectively, of the pumping function unit 10 to make them expand and contract.

The first drive unit 22: is configured of an air pressure actuator 24 which is composed of a servo motor, and an air compression tank 25; and is driven to press the air into the diaphragm 11 through a tube 26.

Practically, in the state where the top end of the tubular joint 15 is interposed into the target person's chest and located at the lower heart part, the first drive unit 22: pushes the diaphragm 11 out from the top end of the tubular joint 15 while pressing the air into the diaphragm 11 under the control of the control unit 21 and simultaneously causes the diaphragm 11 to start flexing to cover and wrap the lower heart part; and stops pressing the air into the diaphragm 11 at the time point where the respective compression balloons 12A to 12D are positioned at the right and left ventricles of the heart.

Figure 5:
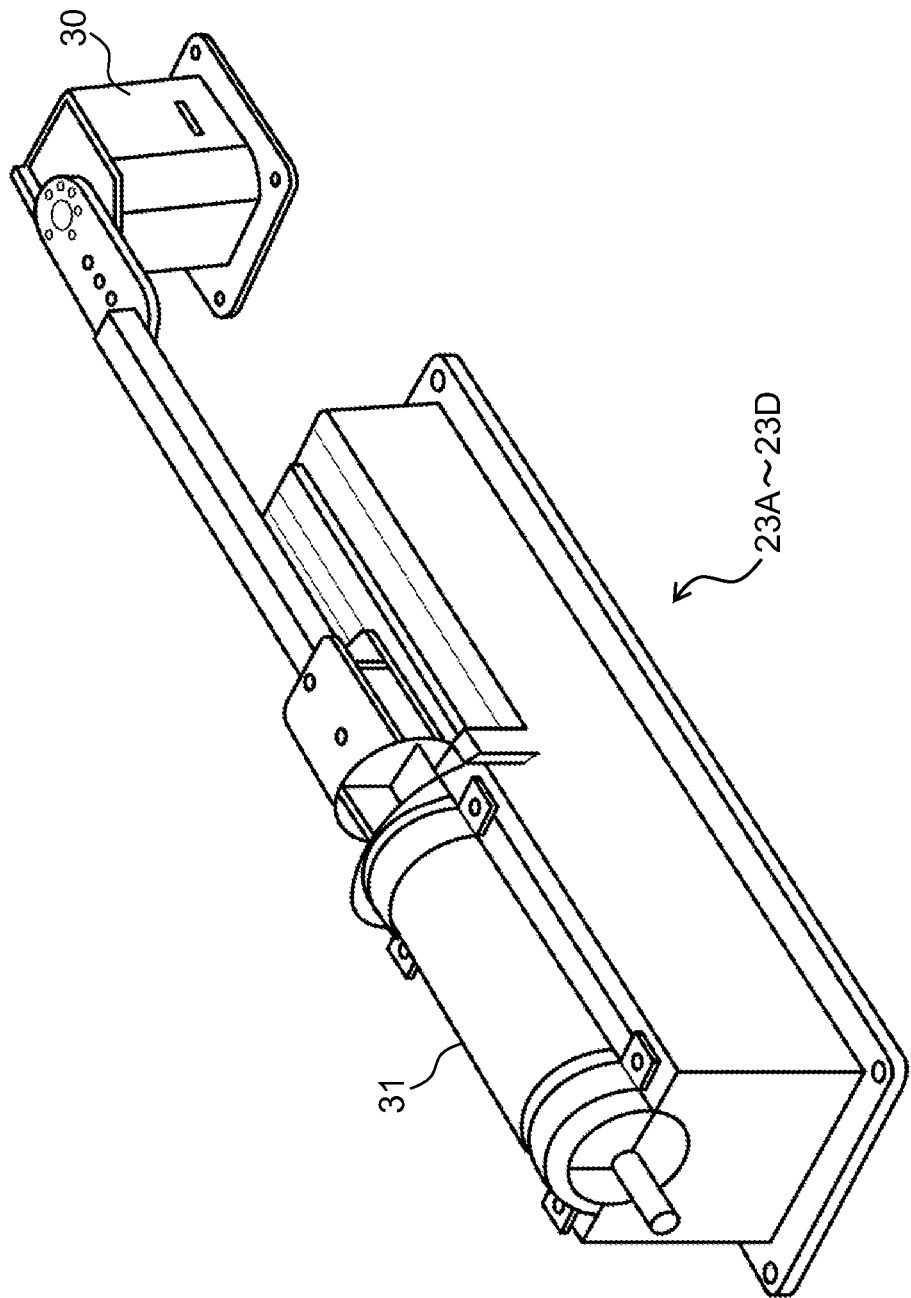
FIG. 5 is a perspective view illustrating a specific configuration of a second drive unit according to this embodiment.

The second drive units 23A to 23D are provided for the left atrium, the left ventricle, the right atrium, and the right ventricle, respectively, corresponding to the compression balloons 12A to 12D. Each of these second drive units 23A to 23D: is configured of, as illustrated in FIG. 5, an actuator (for the left atrium, the left ventricle, the right atrium, and the right ventricle) 30 which is composed of a servo motor, and a cylinder 31 which is filled with water inside and is capable of reciprocating linear motions; and is driven to eject or absorb water to or from the relevant compression balloon 12A to 12D while adjusting a cardiac output support amount according to angular control of the actuator 30.

Practically, each second drive unit 23A to 23D supports the heart's pumping function by adjusting the timing to control compression or relaxation of the right and left atriums and ventricles of the heart while alternately repeating an ejecting operation to fill the relevant compression balloon 12A to 12D with water and make them expand and an absorbing operation to cause the relevant compression balloon 12A to 12D to discharge the water and contract under the control of the control unit 21.

As each second drive unit 23A to 23D ejects water to the relevant compression balloon 12A to 12D, the control unit 21 is designed to adjust a water discharge amount and discharge timing from the corresponding cylinder 31 while servo-controlling each actuator 30 in synchronization with the heart beats, so that the blood in a cardiac output volume of 70 [ml] or more for one output in blood circulation of a general adult male's heart can be repeatedly output from the heart.

Moreover, the cardiac output support apparatus 20 is provided with an optical arterial blood measurement unit 40 capable of non-invasive measurement through the target person's skin surface when the tubular joint 15 is inserted to near the target person's lower heart part, so that a measurement result is sent to the control unit 21 while measuring the target person's pulse rate and arterial oxygen saturation.

The control unit 21 controls each second drive unit 23A to 23D on the basis of the measurement result obtained from the arterial blood measurement unit and independently adjusts the cardiac output and the cardiac output cycle with respect to the respective compression balloons 12A to 12D.

As a result, the cardiac output support apparatus 20 can control the respective compression balloons 12A to 12D in accordance with a blood circulation condition of the target person and suppress degradation of the heart's pumping function (the blood receiving function and the blood sending function) while letting the right and left atriums and ventricles of the heart contract or relax.

Furthermore, the cardiac output support apparatus 20 is provided with a cardiac condition detection unit 41 which has a flexible electrode interposed on an adhesive surface of each compression balloon 12A to 12D relative to the diaphragm 11, so that a detection result is sent to the control unit 21 while detecting a disease condition of the target person's heart.

The control unit 21 controls each second drive unit 23A to 23D on the basis of the measurement result obtained from the cardiac condition detection unit 41 and controls the respective compression balloons 12A to 12D independently in a specified cardiac output cycle and with specified cardiac output.

As a result, the cardiac output support apparatus 20 can control the sequential order and the degree of compression of the respective compression balloons 12A to 12D in accordance with the disease condition of the target person's heart and suppress degradation of the heart's pumping function while letting the right and left atriums and ventricles of the heart contract or relax.

(3) Basic Experiment and its Result

Whether the cardiac output of the blood in one output of the cardiac output volume of 70 [ml] or more of an adult male can be repeatedly supported or not is checked by the following experiment by actually using the cardiac output support apparatus 20 according to the present invention. A model system which simulates a circulatory system is constructed as a heart model by simulating the degree of hardness of an actual heart, blocking blood vessels of a left heart system other than an aorta and a pulmonary vein, and filling the left heart system with water; and also the heart model in which balloons containing water are inserted in a right ventricle is prepared. Valves of this heart model are simulated to prevent a reverse flow by closing the pulmonary vein when compressing the heart.

Figure 6:
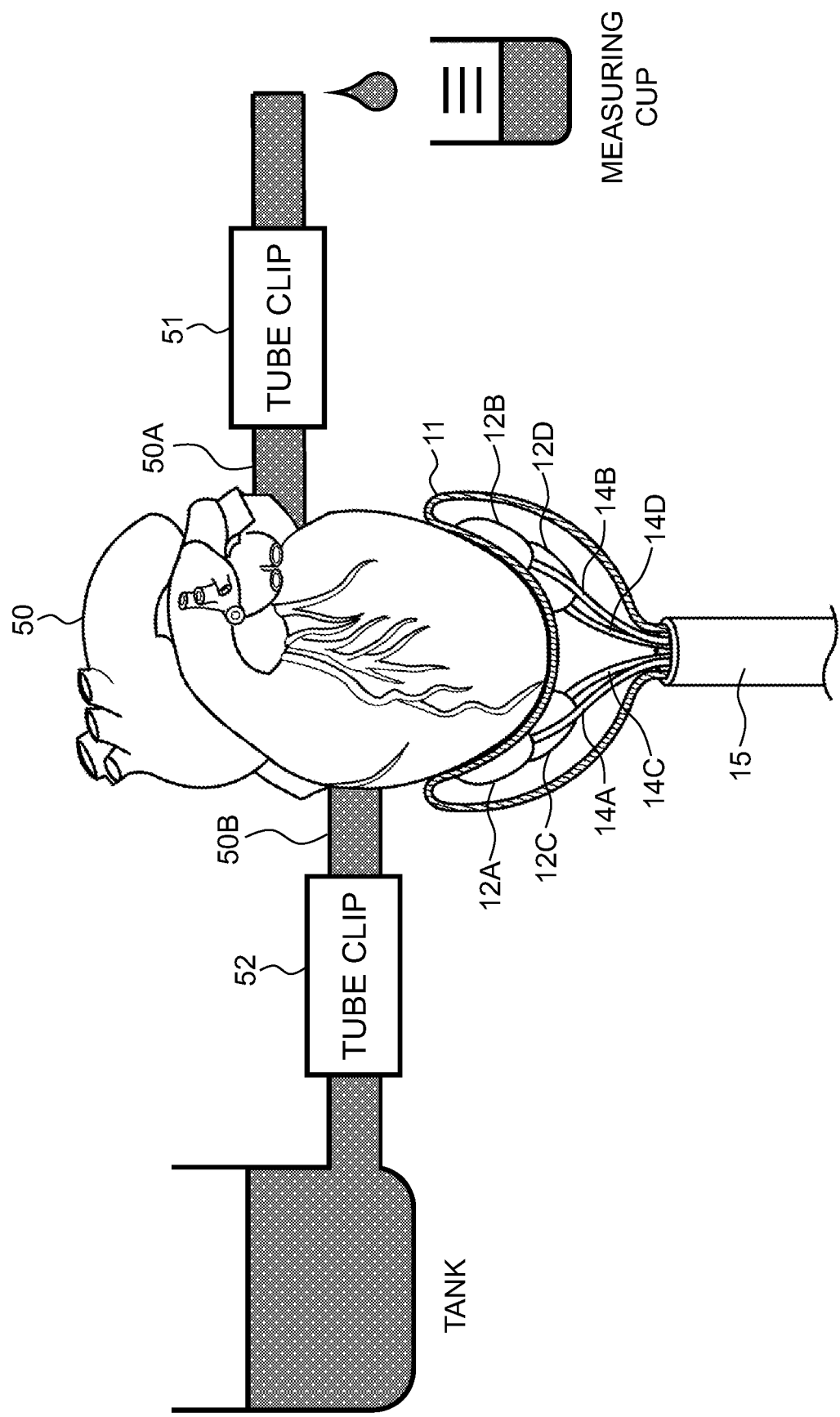
FIG. 6 is a schematic explanatory diagram illustrating a system for driving a heart model in a basic experiment.

Referring to FIG. 6, practically with this heart model 50, an aorta 50A is closed with a tube clip 51, the left heart system is filled with water, and the heart model 50 is caused to expand. Subsequently, a pulmonary vein 50B is closed with a tube clip 52 and the tube clip 51 of the aorta 50A is released. The cardiac output support apparatus 20 according to this embodiment is applied in this state and the respective compression balloons 12A to 12D are compressed against the heart model 50 to cause the water in the heart model 50 to be discharged.

Figure 7:
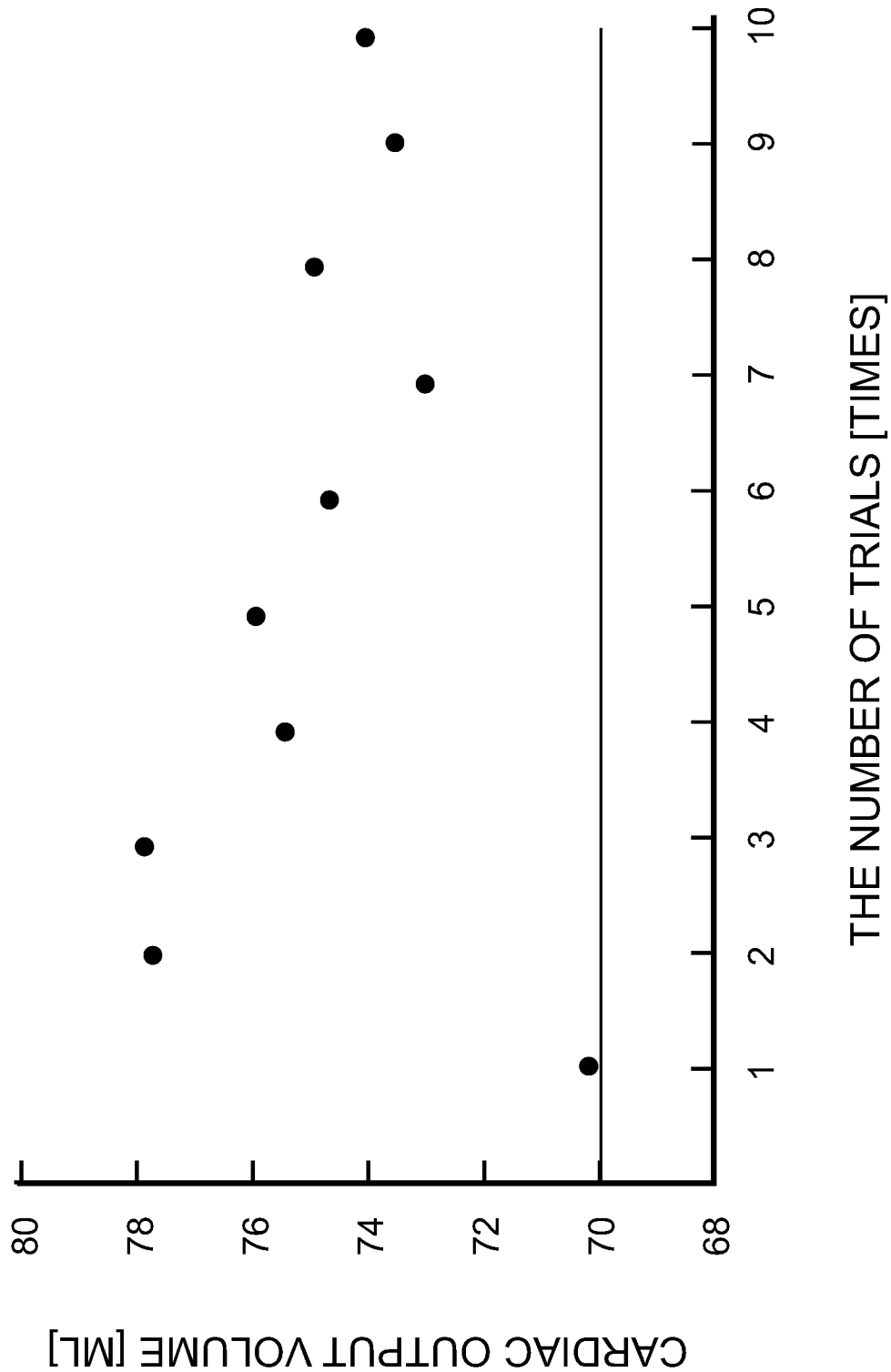
FIG. 7 is a graph showing the result of the basic experiment illustrated in FIG. 6.

As a result of trying a cardiac output support operation by using this cardiac output support apparatus 20 ten times, an amount of water discharged from the heart model 50 was 70 [ml] or more in all the trials as illustrated in FIG. 7. According to this experiment result, it has been confirmed by this experiment result that the cardiac output support apparatus 20 according to this embodiment has the performance capable of sufficiently securing the cardiac output volume by the pumping function of the heart model 50.

Incidentally, if the fluid inside the heart is blood, it is predicted that the blood has high viscosity and can hardly be discharged; however, it has already been confirmed that this can be handled by increasing the amount of water to be supplied to each compression balloon.

(4) Operations According to this Embodiment

Regarding the cardiac output support apparatus 20 with the above-described configuration, after part of the chest corresponding to the lower heart part of the patient whose cardiac output function has deteriorated significantly due to the myocardial infarction is slightly incised, the tubular joint in which the diaphragm 11 and the respective compression balloons 12A to 12D are stuffed is inserted into the incised part and is located at the lower heart part.

In this state, the control unit 21 controls the first drive unit 22 to: push the diaphragm 11 out from the top end of the tubular joint 15 while pressing the air into the diaphragm 11 and causes the diaphragm 11 to start flexing to cover and wrap the lower heart part; and stop pressing the air into the diaphragm 11 at the time point where the respective compression balloons 12A to 12D are positions at the right and left atriums and ventricles of the heart.

Subsequently, the control unit 21 controls the second drive units 23A to 23D to support the heart's pumping function by alternately repeating the ejecting operation to fill the respective compression balloons 12A to 12D with water and make them expand and the absorbing operation to cause the respective compression balloons 12A to 12D to discharge the water and contract.

As a result, the cardiac output support apparatus 20 can cover and wrap the lower heart part with the diaphragm 11 and simultaneously position the respective compression balloons 12A to 12D by increasing the air pressure inside the diaphragm 1 from outside in the state where the target person's chest is incised along the length approximately equal to the diameter of the tubular joint 15 and the tubular joint 15 is inserted into the incised part.

Consequently, if the cardiac output support apparatus 20 is employed, it becomes no longer necessary to incise the target person's chest along the length equal to or longer than the width of the heart; and, therefore, even a doctor who is not a cardiovascular surgery medical specialist can perform the operation and secure the sufficient amount of blood to the heart and it is possible to minimize damage to the target person's heart.

(5) Other Embodiments

Incidentally, this embodiment has described the case where the four compression balloons 12A to 12D corresponding to the right and left atriums and ventricles are pasted on the diaphragm 11 of the pumping function unit 10 and are respectively independently driven in synchronization with the heart beats; however, the present invention is not limited to this example and only either the compression balloons for the left heart (the left atrium and the left ventricle) or the compression balloons for the right heart (the right atrium and the right ventricle) may be driven. As a result, for example, the right heart support and the left heart support may be executed or stopped respectively independently by: performing the support of both the hearts if the patient's condition is bad; and switching to the support of only the left heart if the patient's condition is recovering.

Moreover, this embodiment has described the case where its entire membrane of the diaphragm 11 flexes according to the air pressure, but a material with a very low degree of expansion and contraction (that is, a low modulus of elasticity) is selected; however, the present invention is not limited to this example and a peripheral region of the diaphragm 11 which does not enter into direct contact with the heart when the diaphragm 11 covers and wraps the lower heart part may be formed of a material with flexibility and non-pliability.

As a result, with the cardiac output support apparatus 20, when the respective compression balloons 12A to 12D are filled with the fluid and are made to expand, it is possible to prevent the peripheral region of the diaphragm 11 from expanding and pushing the surroundings of the heart towards outside, and avoid compression to the surroundings of the target person's heart.

Furthermore, this embodiment has described the case where each compression balloon 12A to 12D is configured of a material with flexibility and pliability such as silicone rubber; however, the present invention is not limited to this example and a whole or part of the exposed portion of each respective compression balloon 12A to 12D other than its abutting region in contact with the diaphragm 11 may be formed of a material with flexibility and non-pliability.

As a result, with the cardiac output support apparatus 20, when the respective compression balloons 12A to 12D are filled with the fluid and are made to expand, the respective compression balloons 12A to 12D themselves expand only towards the direction opposite the diaphragm 11; and, therefore, it is possible to prevent the peripheral region of the diaphragm 11 from expanding and pushing the surroundings of the heart towards outside, and avoid compression on the surroundings of the target's heart.

Furthermore, this embodiment has described the case where after a part of the chest corresponding to the target person's lower heart part is slightly incised under the normal surgical operation environment, the tubular joint 15 in which the diaphragm 11 and the respective compression balloons 12A to 12D are stuffed is inserted and located at the lower heart part; however, the present invention is not limited to this example and a freely expandable and contractable mesh-like material whose size is set to fit the external shape of the target person's lower heart part may be used to cover and wrap the lower heart part before inserting the tubular joint 15.

Under the above-described circumstance, a doctor or the like needs to handle the mesh-like material with their fingertips under the environment by X-ray imaging so that coronary arteries of the target person's lower heart part are exposed through gaps in the mesh-like material, in other words, a mesh fabric of the mesh-like material will not cover the coronary arteries. As a result, when the target person's lower heart part which is covered and wrapped with the mesh-like material is then covered and wrapped with the diaphragm 11 and its internal air pressure is increased, it is possible to avoid the occurrence of any damage due to the compression on the coronary arteries of the lower heart part even if the ejecting operation and the absorbing operation by the respective compression balloons 12A to 12D are performed.

Moreover, this embodiment has described the case where the water which is an incompressible fluid is used as the fluid in the respective compression balloons 12A to 12D; however, the present invention is not limited to this example and any liquid other than the water may be used as long as it is the incompressible fluid regarding which safety for the human body can be secured.

Furthermore, this embodiment has described the case where the air is applied as the gas which is pressed into the diaphragm 11; however, the present invention is not limited to this example and any gas such as a helium gas may be used as long as it does not affect the human body.

REFERENCE SIGNS LIST

10: pumping function unit
11: diaphragm
12A to 12D: compression balloons
13: air supply passage
14A to 14D: tubes
15: tubular joint
20: cardiac output support apparatus
21: control unit
22: first drive unit
23A to 23D: second drive units
30: servo motor
31: cylinder
40: arterial blood measurement unit
41: cardiac condition detection unit
50: heart model

The invention claimed is:

1. A cardiac output support apparatus comprising:
a diaphragm that is configured to fit an external shape of a lower heart part of a target person and, wherein the diaphragm is composed of a flexible membrane that is responsive to a gas pressure;
a plurality of compression balloons that are located at specified positions of an inner wall surface of the diaphragm, wherein the compression balloons are positioned opposite to atriums and ventricles of a heart, respectively when the lower heart part is covered and wrapped with the diaphragm;
an air pressure actuator that is configured to press a gas into the diaphragm;

a left actuator and a right actuator that are each configured to eject or absorb a fluid to or from the compression balloons, respectively; and a tubular joint with a hollow part in which the diaphragm and each of the compression balloons are collectively stuffed, wherein the diaphragm is stuffed into the hollow part of the tubular joint with reference to a mark assigned to a top end of the tubular joint by defining a positional relationship between respective compression balloons, wherein, in a state where the top end of the tubular joint is interposed in a chest of the target person, the tubular joint is located at the lower heart part, and the mark is positioned in conformity with the atriums and the ventricles, the air pressure actuator is configured to:

push the diaphragm out from the top end of the tubular joint while the gas is pressed into the diaphragm, simultaneously cause the diaphragm to start flexing to cover and wrap the lower heart part, and stop pressing the gas into the diaphragm at a time point where the compression balloons are positioned at the atriums and the ventricles of the heart, respectively; and wherein the left actuator and the right actuator are each configured to support a pumping function of the heart by alternately repeating:

an ejecting operation that fills each of the compression balloons with the fluid, wherein the ejecting operation causes each compression balloon to expand, and an absorbing operation that causes each respective compression balloon to discharge the fluid and contract.

2. The cardiac output support apparatus according to claim 1, wherein a peripheral region of the diaphragm which does not enter into direct contact with the heart when covering and wrapping the lower heart part is formed of a material having flexibility and non-pliability.

3. The cardiac output support apparatus according to claim 2, wherein a whole or part of an exposed portion of each compression balloon other than its abutting region in contact with the diaphragm is formed of a material having flexibility and non-pliability.

4. The cardiac output support apparatus according to claim 1,
wherein each of the left actuator and the right actuator are configured to independently adjust a cardiac output and a cardiac output cycle with respect to each compression balloon based on a pulse rate and arterial oxygen saturation of the target person.

5. The cardiac output support apparatus according to claim 1,
wherein each of the left actuator and the right actuator are configured to independently control each compression balloon in a specified cardiac output cycle and with a specified cardiac output based on a disease condition of the heart of the target person.

6. The cardiac output support apparatus according to claim 1,
wherein a freely expandable and contractable mesh-like material whose size is set to fit the external shape of the lower heart part of the target person is made to cover and wrap the lower heart part in such a manner that coronary arteries are exposed from gaps under an environment of X-ray imaging; and the diaphragm is made to further cover and wrap a surface of the freely expandable and contractable mesh-like material.

7. The cardiac output support apparatus according to claim 1, wherein the air pressure actuator is comprised of a servo motor and an air compression tank.

8. The cardiac output support apparatus according to claim 1, wherein the left actuator and the right actuator are each composed of a servo motor and a cylinder which is filled with water inside.

* * * * *